United States Patent
Gattu et al.

(10) Patent No.: US 11,334,057 B2
(45) Date of Patent: May 17, 2022

(54) ANOMALY DETECTION FOR PREDICTIVE MAINTENANCE AND DERIVING OUTCOMES AND WORKFLOWS BASED ON DATA QUALITY

(71) Applicant: GE Inspection Technologies, LP, Lewistown, PA (US)

(72) Inventors: Jagadish Gattu, Randolph, MA (US); Nimrod Ohad, Schenectady, NY (US)

(73) Assignee: WAYGATE TECHNOLOGIES USA, LP, Houston, TX (US)

( * ) Notice: Subject to any disclaimer, the term of this patent is extended or adjusted under 35 U.S.C. 154(b) by 99 days.

(21) Appl. No.: 16/747,721

(22) Filed: Jan. 21, 2020

(65) Prior Publication Data

US 2020/0241517 A1    Jul. 30, 2020

Related U.S. Application Data

(60) Provisional application No. 62/797,076, filed on Jan. 25, 2019.

(51) Int. Cl.
*G05B 23/02* (2006.01)
*G06Q 50/08* (2012.01)
*G06Q 50/04* (2012.01)

(52) U.S. Cl.
CPC ..... *G05B 23/0235* (2013.01); *G05B 23/0272* (2013.01); *G05B 23/0281* (2013.01); *G05B 23/0283* (2013.01); *G06Q 50/04* (2013.01); *G06Q 50/08* (2013.01)

(58) Field of Classification Search
CPC ............ G05B 23/0235; G05B 23/0283; G05B 23/0281; G05B 23/0272; Y02P 90/30
See application file for complete search history.

(56) References Cited

U.S. PATENT DOCUMENTS

| | | | |
|---|---|---|---|
| 6,181,975 B1 * | 1/2001 | Gross | G05B 23/0254 700/29 |
| 6,408,953 B1 | 6/2002 | Goldman et al. | |
| 2004/0078171 A1 * | 4/2004 | Wegerich | G05B 23/0254 702/188 |
| 2007/0010900 A1 | 1/2007 | Kavaklioglu et al. | |
| 2012/0306638 A1 * | 12/2012 | Karaffa | G05B 19/0425 340/517 |
| 2016/0019776 A1 * | 1/2016 | Advani | G06F 16/24568 340/526 |
| 2016/0260180 A1 | 9/2016 | Vasquez et al. | |

(Continued)

*Primary Examiner* — Kenneth M Lo
*Assistant Examiner* — Jonathan Michael Skrzycki
(74) *Attorney, Agent, or Firm* — Mintz Levin Cohn Ferris Glovsky and Popeo, PC; Lisa Adams

(57) ABSTRACT

Systems, methods, and computer readable storage mediums for performing sensor health monitoring are described. The method includes verifying data quality and suppressing alert generation using machine learning techniques to identify whether two anomalies generated by an asset monitoring system are related. The method can include receiving data characterizing measurement data acquired by a sensor coupled to an industrial asset. An anomalous data sample within the received data can be identified and removed from the anomalous data sample. A new sample of the removed data sample can be estimated using interpolation and the new sample can be assessed. Maintenance analysis can be performed based on the assessed, estimated new sample.

14 Claims, 2 Drawing Sheets

(56) References Cited

U.S. PATENT DOCUMENTS

| | | | |
|---|---|---|---|
| 2016/0305848 A1* | 10/2016 | Boggio | G06Q 10/20 |
| 2018/0284735 A1* | 10/2018 | Celia | G05B 23/0264 |
| 2018/0299878 A1 | 10/2018 | Cella et al. | |
| 2019/0003929 A1 | 1/2019 | Shapiro et al. | |
| 2019/0188584 A1* | 6/2019 | Rao | G06Q 10/00 |
| 2019/0235481 A1* | 8/2019 | Takigawa | G05B 23/024 |
| 2020/0201312 A1* | 6/2020 | Whitehead | G01D 3/08 |

* cited by examiner

ANOMALY DETECTION FOR PREDICTIVE MAINTENANCE AND DERIVING OUTCOMES AND WORKFLOWS BASED ON DATA QUALITY

CROSS-REFERENCE TO RELATED APPLICATIONS

This application claims priority to U.S. Provisional Application No. 62/797,076 filed on Jan. 25, 2019, the disclosure of which is hereby incorporated by reference in their entirety.

BACKGROUND

Industrial equipment can be complex and can be prone to different types of complex modes of failure. The equipment can include a multitude of sensors that can be used to monitor operation of the equipment. One method of utilizing sensor data includes developing rule-based detection schemes that can be used to monitor performance of the equipment. Based on the rules implemented within the detection schemes, the sensors, or a controller monitoring the sensors, can determine if the equipment is operating within acceptable parameters.

SUMMARY

In an aspect, systems for sensor health monitoring are provided. The systems can perform sensor health monitoring by verifying data quality and suppressing alerts via machine learning techniques in order to identify whether two anomalies generated by an asset monitoring system are related is described. Related apparatus, systems, techniques and articles are also described.

In another aspect, a method includes receiving data characterizing measurement data values from acquired by a sensor coupled to an industrial asset; identifying an anomalous data sample within the received data and removing the anomalous data sample; estimating, using interpolation, a new sample of the removed data sample; and assessing the estimated new sample.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

Like reference symbols in the various drawings indicate like elements.

DETAILED DESCRIPTION

Oil and gas industrial environments can utilize asset monitoring and diagnosis systems to monitor the operating conditions of one or more, and in some cases, thousands of assets. In asset monitoring and diagnosis systems including sensors, detection of anomalies in sensor measurements can be desirable. Monitoring asset operation can include efficient management of alerts generated in response to anomaly detection. Overall system performance can be determined by the health status of sensors. Sensor and/or instrument health can be relied on by predictive maintenance analyses and/or analytic solutions to diagnose asset health, in some cases, before problems can arise.

Predictive diagnostics to diagnose the health of an asset can, however, include a chance that the asset is misdiagnosed. Further, predictive maintenance analyses and/or analytic solutions not accounting for sensor health can incorrectly misdiagnose assets that are otherwise operating properly. In some cases, duplicate diagnoses can be made, which each can trigger an alert. In either case, an alert can be generated notifying users of the asset monitoring and diagnosis systems of a potentially anomalous asset, but uncertainty can be included in the predictive maintenance analysis diagnosis generating the alert of a potential future failure. Furthermore, duplicate alerts can exhaust user bandwidth and can render an asset monitoring system unusable.

It can be desirable to monitor sensor health to prevent asset health misdiagnosis. And it can be desirable to suppress duplicate alerts resulting from related diagnoses. Some aspects of the current subject matter can facilitate sensor health monitoring by verifying data quality and/or duplicate alert suppression by utilizing machine learning to identify whether anomalies generated by an asset monitoring system are related, for example, two anomalies.

Figure 1:
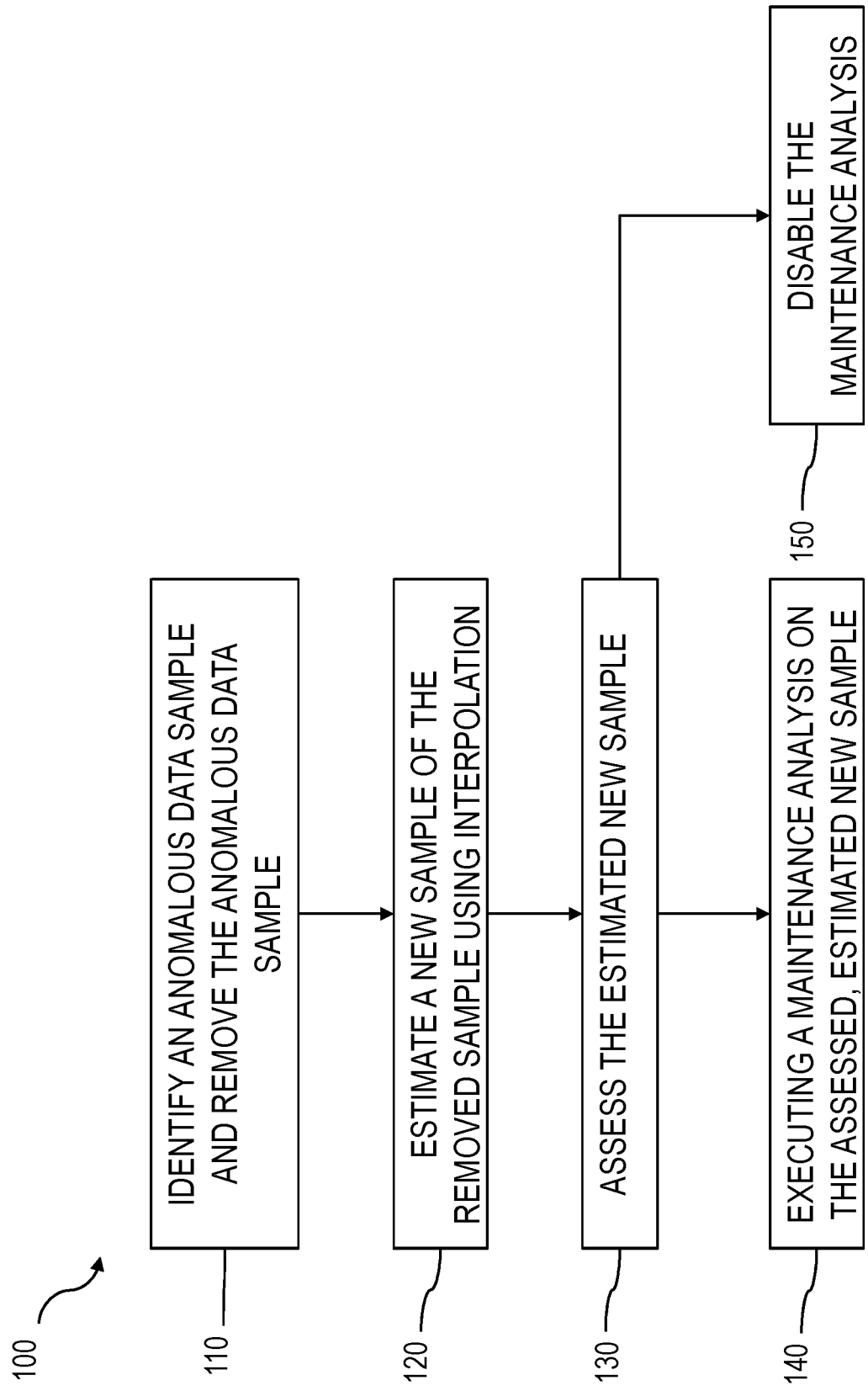
FIG. 1 is a process flow diagram illustrating an example implementation of a process for outcome derivation.

FIG. 1 is a process flow diagram illustrating an example process 100 for outcome derivation for predictive analytics. Utilizing data quality rules can facilitate sensor health monitoring by verifying data quality and/or generating an alert when data quality can be determined to be bad. By verifying data quality and duplicate alert suppression by utilizing machine learning, identification of whether two or more anomalies generated by an asset monitoring system are related can be achieved.

At 110, anomalous data samples can be identified and removed. The data samples can be processed for anomalous data samples in a data quality engine. The data quality engine can utilize data quality or data validation rules to identify anomalous data samples. When a data quality rule is violated (e.g., the data includes bad data quality and thus causes a data quality rule to be broken), a generated alert can identify the start and end of the data quality issue. The generated alert can identify individual data points which have violated the data quality rule. For example, a data validation rule can verify whether the datatype of a signal or measurement received from the sensor matches the datatype of a pre-determined data tag, the signal or measurement received from the sensor contains NULL and/or empty values, and/or the signal or measurement received from the sensor is missing for more than three samples.

For example, a mean variance rule can verify the rate of change of the signal and whether there is a change in the mean value and variance for the rate of change. When the change in mean and variance is considerable, exceeds a threshold, and/or is outside of a predetermined range, the mean variance rule can be violated. For example, an out range rule can verify whether the signal values are within valid operating range. For example, a flat line rule can receive a flat line number and identify how many repeating signals can occur before a signal can be considered flat lined. The flat line rule can receive a flat line precision range and values within the flat line precision range can be considered as repeating signal values. Data samples violating data quality rules can be identified as anomalous or problematic, and the identified data samples can be removed. In some implementations, metadata identifying the problem associated with anomalous data can be stored along with the time series data in a way that can maintain the size of the time series data (e.g., without significantly increasing the space required to store the time series data).

At 120, removed data samples can be estimated using missing data estimation techniques. When a data sample is removed, it can be desirable to estimate the missing data to continue estimating asset operation. Estimating missing data samples can allow asset monitoring even when data can be sparse and/or intermittently lost. Missing data can be estimated using missing data estimation techniques, such as interpolation and/or extrapolation. Interpolation can construct new data samples within the range of a discrete set of existing data. Extrapolation can construct new data samples outside the range of the discrete set of existing data. A user can select the specific technique for data estimation, such as linear, cubic, spline, and/or the like. Other data estimation techniques can include multiple imputation, k-nearest neighbors, gradient boosting (e.g., XGBoost), random forest, and/or the like.

At 130, estimation of removed data can be assessed. For example, the estimated data can be assessed by partitioning a known dataset into training and/or validation sets and evaluating the fit of the estimated data to the known dataset using f-test, z-test, t-test, confidence intervals (e.g., confidence bands), combinations thereof, and/or the like. The fit of the estimated data can prevent exhausting user bandwidth understanding the root cause of an alert when the problem can be in the data.

When estimated data can be assessed as a good fit, for example when an estimate quality metric exceeds a pre-determined threshold value or an error metric is below a pre-determined threshold value, at 140, a maintenance analysis on the data samples including the estimated data can be executed. If an out of range and/or not an error (NaN) test failure is observed, rules down the line that use these tags can generate an alert for data quality violations, but can use the estimated data to execute the maintenance rules that are dependent on these tags. For example, threshold rules, anomaly detection, and/or the like can rely on the tags. By performing analytics using the estimated data values, the analytic performance can be improved. Further, identifying the data quality and estimating the missing data can help in detecting specific failure modes for the asset because detecting specific failure modes can require the ability to assess trends in individual sensor data.

When estimated data can be assessed as bad data, at 150, a maintenance analysis on the data samples can be suspended. If an out of range and/or NAN test failure is observed, rules down the line can generate an alert for the data quality violations, and the maintenance rules that can depend on these tags can be suspended. For example, threshold rules, anomaly detection, and/or the like can rely on the tags. By suspending maintenance analytics for poorly estimated data values, scenarios in which the analytic might produce a poor result can be avoided.

In some implementations, when a threshold rule is violated continuously, detecting that the same rule has been violated multiple times, and that multiple alerts should not be continuously generated can be performed. But in the case of predictive maintenance analyses based on machine learning models, the violation can be generated by patterns in several signals. In such a case, there can be no precise rule to detect that two distinct patterns, each generating a separate alert, can correspond to the same problem. Machine learning techniques can be utilized to determine when two diagnoses, based on two separate patterns, are the same diagnosis. Based on this determination, new alert generation can be suppressed so that the user is alerted once, rather than multiple, in some cases hundreds of times, for a specific problem.

In some implementations, generating an alert can combine fuzzy logic and machine learning to identify whether two anomalies generated by an anomaly detection model are the same. The signals contributing to the first anomaly can be analyzed and the pattern of the contributing signals can be compared to the pattern of contributing signals in the second anomaly. If the patterns are a match (using the combination of fuzzy logic and machine learning), then the second anomaly cannot generate a new alert. Instead, the second anomaly information can be added to the alert corresponding to the first anomaly. Thus, one alert can be generated for two separate anomalies identified at two distinct timestamps.

In some implementations, when using predictive diagnostics to diagnose the health of an asset, the nature of the predictive diagnosis can include a chance that the health of the asset is misdiagnosed. As a result, an engineer can be required to assess the validity of the diagnosis. In order to assess the validity, the engineer can look at the overall health of the asset. However, this information can be spread amongst several different systems, such as Computerized Maintenance Management Software (CMMS) and Enterprise Asset Management (EAM), vibration monitoring systems, lube oil analysis, calibration information, and/or the like. This can create a cumbersome, time consuming process to assess a diagnosed problem. It can be desirable for this contextual information, needed for problem assessment, to be presented in one place, for example, in a single pane of glass. But, to reduce user effort and decrease time required to address the diagnosed problem, the contextual information may need to be presented in the context of the current problem.

In some implementations, a layered approach can present the relevant asset health information in a single analysis pane. This approach can enable a user to see maintenance analysis information, varying past alerts, and/or previous failures in a single screen. For example, data quality alerts can be highlighted on a single time series tag. A maintenance analysis record can be displayed on a separate axis with a common time stamp. And, if there is a calibration record, it can be shown as corresponding to a single tag. But, anomalies and failure modes can be displayed as bands within the time series tags, and can highlight only the contributing tags. By filtering the tags to display only the contributing tags, the scope of information displayed to the user can be reduced. And, the maintenance analysis records, which can apply to the entire asset, can be displayed in a separate asset within the same time window giving an overall context to the user.

In some implementations where predictive maintenance analyses can generate an alert about a potential future failure of an oil and gas industrial asset, uncertainty can be included in the diagnosis. Accurate maintenance analysis records and data can be desirable because, for example, shutting down a compressor can be a multi-million dollar decision. As a result, it can be desirable for the uncertainty in a diagnosis to be minimized. But confidence in the existence of a problem can take months to develop. Even though relevant information exists, analysis at scale can be cumbersome. For example, there can be thousands of maintenance records, root cause analysis reports, manuals, and/or the like. It can be desirable to use this data to help an engineer find relevant information that can increase the rate of investigation. It can be cumbersome to assess the validity of a predictive maintenance analysis diagnosis. And searching through billions of structured and unstructured time series data points can be cumbersome. But it can be desirable to utilize this data to find relevant information that can speed up investigations.

In some implementations, natural language based search can be utilized for knowledge management of unstructured records and/or manuals. This can make search easy for a user to find relevant information when searching millions of data records. Machine learning can be utilized to identify past tests or thresholds which have failed and have been determined to match a current problem. Then machine learning can be utilized to identify the matching past problems, including any tests or thresholds which have failed and recommend the identified past problems as the top recommendations for a current problem. Fixes to the past problems corresponding to the current problem can be utilized to efficiently manage alerts. Machine learning can be used to process past time series signals, which can be searched to identify patterns that can be determined to match the current tests or thresholds which have failed. Maintenance analysis actions from the past can be correlated with the current data and can provide a clear idea of past failures that occurred when similar problems were identified.

In some implementations, predictive maintenance analysis solutions can use physics or statistics based models and/or rules to predict the health of an asset. Updating models due to process changes and/or diagnosis false positives can include a significant cost and can be cumbersome to the user. It can be desirable to maintain the models based on process conditions and/or when a diagnosis is incorrect.

In some implementations, unsupervised learning can update predictive models as process conditions change. Smart recommendations can learn whether a diagnosis was correct or incorrect. This information can be used to update the model. For example, the next time a problem is diagnosed, the diagnosis can be more accurate. For process related updates, data can be continuously fed into the model. Whenever the data cannot fit the confidence bands of the model, the model can trigger recalibration. This can result in automatically updating the model. When the user analyzes a problem and specifies that the diagnosis is a false positive, this information can be forwarded to the model. Similarly, to fix the issue, the recommendation due to a synchronization with the work order can be considered to be a true diagnosis. The recommendation can send this information back to the machine learning model and can use this information for reinforced learning of the model. As a result, the model can automatically update.

In some implementations, when a diagnosis is made, operation of the machine undergoing analysis can be modified. For example, when a turbine is diagnosed with anomalous vibrations, the rotation speed of the turbine can be modified in order to correct or address the anomalous behavior. For example, operation of the turbine may be terminated in order to perform maintenance. Other modifications are possible.

Figure 2:
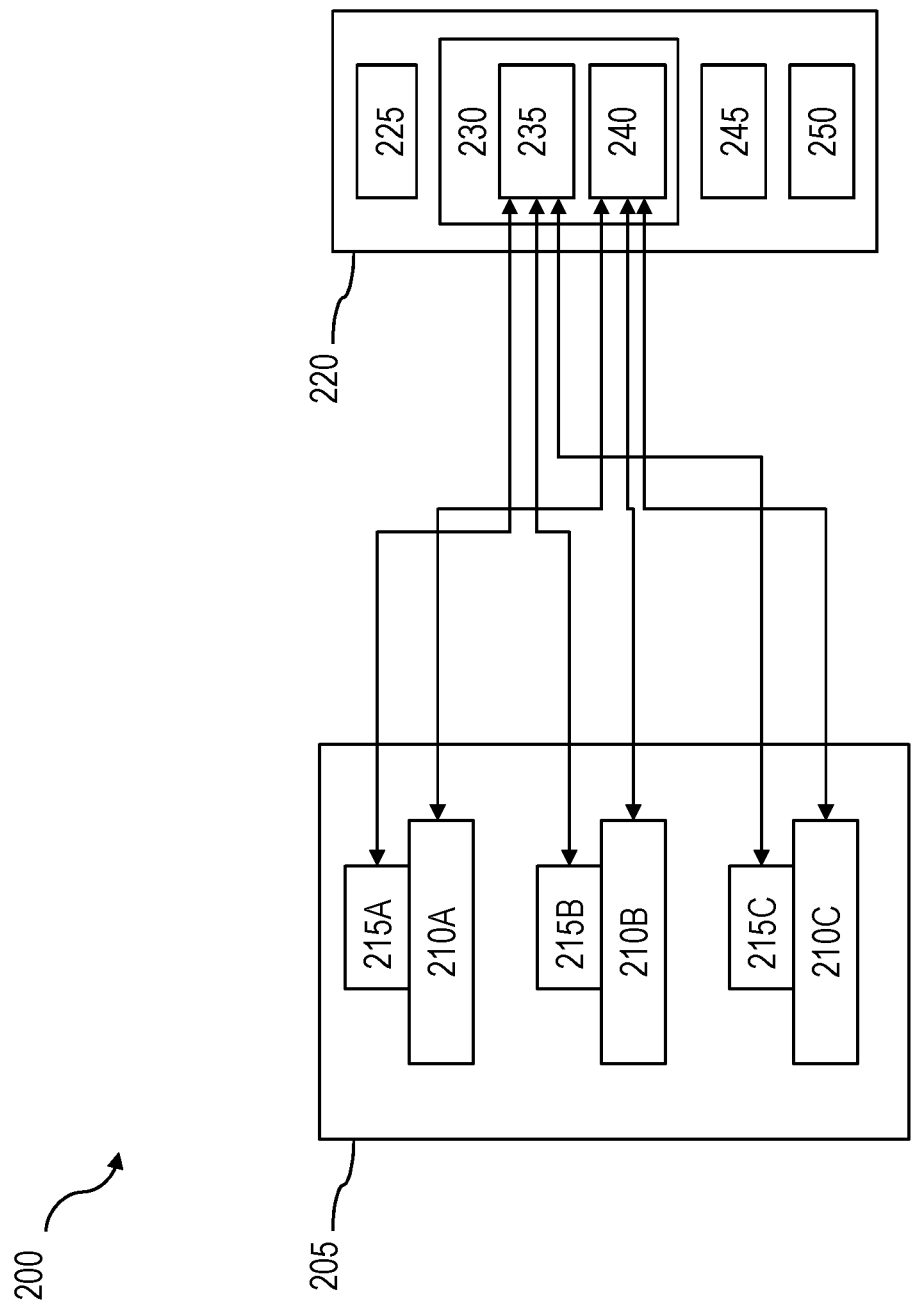
FIG. 2 is a system diagram illustrating a system for sensor health monitoring.

FIG. 2 is a diagram illustrating a system 200 for sensor health monitoring. The system 200 includes an industrial environment 205, such as an oil and gas industrial environment. The industrial environment 205 includes a plurality of industrial assets, shown as industrial asset 210A, 210B, and 210C, which can be collectively referred to as industrial assets 210. The industrial assets can include a variety of equipment or machinery used in a particular industrial domain. For example, the industrial assets 210 can include compressors, pumps, pump motors, heat exchangers, turbines, turbomachinery, or the like. The industrial environment 205 also includes sensors coupled to the plurality of industrial assets 210. The sensors, shown as sensors 215A, 215B, and 215C can be collectively referred to as sensors 215. The sensors 215 can include sensors configured to generate data signals or measurements associated with a vibration, a rotation, an acceleration, an emission, or the like of the industrial assets 210.

As shown in FIG. 2, the system 200 also includes a computing device 220. The computing device 220 can be communicatively coupled to the industrial assets 210 and to the sensors 215. In some embodiments, any of the computing devices 220, the industrial assets 210, and/or the sensors 215 can be coupled via a wired communication means. In some embodiments, the computing device 220 can be coupled to any of the computing devices 220, the industrial assets 210, and/or the sensors 215 via a wireless communication means. In some embodiments, the computing device 220 can be coupled to any of the computing devices 220, the industrial assets 210, and/or the sensors 215 via a network, such as a virtual private network configured to share data within the industrial environment 205.

The computing device 220 includes a data processor 225, a predictive analytic system 230, a memory 245, and a display 250. The predictive analytic system 230 can include computer-readable instructions, rules, and predictive models which when executed by the data processor 225 monitor sensor health by performing the process 100 described in relation to FIG. 1. The predictive analytic system 230 includes a data quality engine 235 and a controller 240. The data quality engine 235 is coupled to the sensors 215 and can receive measurement data from the sensors for use in monitoring the operation and health of the sensors 215 and the assets 210. The data quality engine 235 can include one or more rules used to evaluate and validate the quality of the measurement signals or data received from the sensors 215.

The predictive analytic system 230 also includes a controller 240. The controller 240 is coupled to each of the industrial assets 210 and can be configured to control an operation of the industrial asset 210 based on the maintenance analysis executed by the data quality engine 235 in operation 140 of FIG. 1. The controller 240 can be configured to modify operations such as powering on or powering off the industrial asset 210, adjusting a rate of speed of the industrial asset 210, modifying a frequency of operation of the industrial asset 210, or the like.

The computing device 220 also includes a memory 245. The memory 245 can include a database or other similar data structure which can be used to store computer-readable instructions, data quality or data validation rules, predictive models, as well as sensor data received from the sensors 215 and configuration data associated with controlling the operation of the industrial asset 210 using the controller 240.

The computing device 220 also includes a display 250. The display 250 can include a graphical user interface (not shown). The display 250 can provide the results of the maintenance analysis, any alerts generated by the predictive analytic system 230, and operational data associated with the operation of the industrial asset 210 and/or the sensor 215 to a user or operator of the predictive analytic system 230.

The subject matter described herein can provide many technical advantages. For example, it can facilitate sensor health monitoring by verifying data quality and duplicate alert suppression by utilizing machine learning to identify whether two anomalies generated by an asset monitoring system are related One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method comprising:
   receiving data characterizing measurement data values acquired by a sensor coupled to a compressor;
   identifying a first data sample within the received data, the first data sample including at least one measurement data value having an anomalous datatype, wherein identifying the first data sample includes applying at least one data validation rule to the received data, the at least one data validation rule configured to verify a rate of change in a mean value of the measurement data values and to generate an alert in response to the first data sample failing the data validation rule;
removing the first data sample;
estimating, using at least one data estimation technique, a second data sample to replace the first data sample, the at least one data estimation technique including performing gradient boosting on the removed first data sample; and
assessing the estimated second data sample by evaluating a fit between the estimated second data sample with respect to a dataset of known measurement data values, the fit determined based on applying an f-test to the second data sample and the dataset of known measurement data values wherein responsive to determining the fit of the estimated second data sample fails the f-test,
generating an alert including at least one tag identifying the failing test; with:
generating the alert including at least one tag identifying the failing test;
executing a maintenance analysis on the assessed, estimated second data sample based on the at least one tag; and
providing the alert and a result of the maintenance analysis for display, wherein the alert is displayed on a single time-series tag on a first axis with a first time stamp and the result of the maintenance analysis is displayed on a second axis, separate from the first axis, with a second time stamp, the first time stamp and the second time stamp being identical.

2. The method of claim 1, wherein the sensor is affixed to the compressor in an oil and gas industrial environment and the received data further characterizes a state of health of the compressor.

3. The method of claim 2, wherein the sensor is included in a sensor health monitoring system associated with the oil and gas industrial environment and the received data further characterizes a state of health of the sensor.

4. The method of claim 1, wherein the at least one data validation rule is included in a plurality of data validation rules configured to verify a datatype of the one or more anomalous datatypes in the measurement data values, an empty data value within the measurement data values, a presence of repeating measurement data values, or an absence of three or more measurement data values.

5. The method of claim 1, wherein the at least one data estimation technique is selected from a plurality of data estimation techniques including linear, cubic, spline, multiple imputation, k-nearest neighbors, or random forest data estimation.

6. The method of claim 1, wherein the generation of alerts is suppressed based on evaluating the alert and the fit using one or more machine learning models trained in a machine learning process utilizing historical measurement data values associated with the compressor as training data for the one or more machine learning models.

7. The method of claim 6, wherein the one or more machine learning models are further configured to generate a combined alert responsive to determining the fit of two or more estimated second data samples fail one or more tests or thresholds identified as failing previously, wherein the two or more estimated second data samples failing the one or more tests or thresholds include identical failure patterns.

8. The method of claim 6, wherein the one or more machine learning models can be recalibrated and updated based on the fit of two or more estimated second data samples failing one or more tests or thresholds, wherein the training data includes false positive results of a maintenance analysis executed on the assessed, estimated second data.

9. The method of claim 1, further comprising, modifying an operation of the compressor based on executing a maintenance analysis on the assessed, estimated second data sample.

10. A system comprising:
a data processor, a display, a controller, and a memory storing non-transitory, computer-readable instructions, which when executed cause the data processor to perform operations including
receiving data characterizing measurement data values acquired by a sensor communicatively coupled to a compressor, the sensor generating measurement data values,
identifying a first data sample within the received data, the first data sample including at least one measurement data value having an anomalous datatype, wherein identifying the first data sample includes applying at least one data validation rule to the received data, the at least one data validation rule configured to verify a rate of change in a mean value of the measurement data values and to generate an alert in response to the first data sample failing the data validation rule,
removing the first data sample,
estimating, using at least one data estimation technique, a second data sample to replace the first data sample, the at least one data estimation technique including performing gradient boosting on the removed first data sample, and
assessing the estimated second data sample by evaluating a fit between the estimated second data sample with respect to a dataset of known measurement data values, the fit determined based on applying an f-test to the second data sample and the dataset of known measurement data values wherein responsive to determining the fit of the estimated second data sample fails the f-test,
generating an alert including at least one tag identifying the failing test; with:
generating the alert including at least one tag identifying the failing test;
executing a maintenance analysis on the assessed, estimated second data sample based on the at least one tag, and
providing the alert and a result of the maintenance analysis for display, wherein the alert is displayed on a single time-series tag on a first axis with a first time stamp and the result of the maintenance analysis is displayed on a second axis, separate from the first axis, with a second time stamp, the first time stamp and the second time stamp being identical.

11. The system of claim 10, wherein the sensor is affixed to the compressor in an oil and gas industrial environment and the received data further characterizes a state of health of the compressor.

12. The system of claim 11, wherein the sensor is included in a sensor health monitoring system associated with the oil and gas industrial environment and the received data further characterizes a state of health of the sensor.

13. The system of claim 10, wherein the at least one data validation rule is included in a plurality of data validation rules configured to verify a datatype of the measurement data values, an empty data value within the measurement data values, a presence of repeating measurement data values, or an absence of three or more measurement data values.

14. A non-transitory computer readable storage medium containing program instructions, which when executed by at least one data processor causes the at least one data processor to perform operations comprising:
receiving data characterizing measurement data values acquired by a sensor communicatively coupled to a compressor,
identifying a first data sample within the received data, the first data sample including at least one measurement data value having an anomalous datatype, wherein identifying the first data sample includes applying at least one data validation rule to the received data, the at least one data validation rule configured to verify a rate of change in a mean value of the measurement data values and to generate an alert in response to the first data sample failing the data validation rule,
removing the first data sample,
estimating, using at least one data estimation technique, a second data sample of the removed first data sample, the at least one data estimation technique including performing gradient boosting on the removed first data sample,
assessing the estimated second data sample by evaluating a fit between the estimated second data sample with respect to a dataset of known measurement data values, the fit determined based on applying an f-test to the second data sample and the dataset of known measurement data values wherein responsive to determining the fit of the estimated second data sample fails the f-test,
generating an alert including at least one tag identifying the failing test; with:
generating the alert including at least one tag identifying the failing test;
executing a maintenance analysis on the assessed, estimated second data sample based on the at least one tag,
providing the alert and a result of the maintenance analysis via a display, wherein the alert is displayed on a single time-series tag on a first axis with a first time stamp and the result of the maintenance analysis is displayed on a second axis, separate from the first axis, with a second time stamp, the first time stamp and the second time stamp being identical, and
controlling, via a controller coupled to the at least one data processor and the sensor, an operation of the compressor based on the result of the maintenance analysis.

* * * * *